(12) United States Patent
Hauptmann et al.

(10) Patent No.: US 10,195,449 B2
(45) Date of Patent: Feb. 5, 2019

(54) HOUSING FOR A MEDICAL IMPLANT WITH AN ELECTRICAL TRANSMISSION

(71) Applicant: Forschungszentrum Juelich GmbH, Juelich (DE)

(72) Inventors: Christian Hauptmann, Starnberg (DE); Sven Juergen Grob, Duesseldorf (DE)

(73) Assignee: Forschungszentrum Juelich GmbH, Juelich (DE)

( * ) Notice: Subject to any disclaimer, the term of this patent is extended or adjusted under 35 U.S.C. 154(b) by 0 days.

(21) Appl. No.: 15/575,873

(22) PCT Filed: May 27, 2016

(86) PCT No.: PCT/EP2016/062037
§ 371 (c)(1),
(2) Date: Nov. 21, 2017

(87) PCT Pub. No.: WO2016/189147
PCT Pub. Date: Dec. 1, 2016

(65) Prior Publication Data
US 2018/0221670 A1    Aug. 9, 2018

(30) Foreign Application Priority Data

May 28, 2015   (DE) .................. 10 2015 108 467

(51) Int. Cl.
*H02G 3/08*   (2006.01)
*A61N 1/375*   (2006.01)
(Continued)

(52) U.S. Cl.
CPC ......... *A61N 1/3756* (2013.01); *A61N 1/3754* (2013.01); *A61N 1/37514* (2017.08);
(Continued)

(58) Field of Classification Search
CPC .............. A61N 1/3756; A61N 1/37514; A61N 1/3754; A61N 1/378; A61N 1/3968;
(Continued)

(56) References Cited

U.S. PATENT DOCUMENTS

| 5,406,444 | A | * | 4/1995 | Selfried | ................... | H01G 4/35 |
| | | | | | | 174/152 GM |
| 5,751,539 | A | * | 5/1998 | Stevenson | ............ | A61N 1/3754 |
| | | | | | | 174/143 |
| 5,825,608 | A | * | 10/1998 | Duva | ....................... | H01G 4/35 |
| | | | | | | 174/143 |
| 6,008,980 | A | | 12/1999 | Stevenson et al. | | |

(Continued)

FOREIGN PATENT DOCUMENTS

| DE | 10 2008 028 742 A1 | 1/2010 |
| DE | 10 2014 009 136 A1 | 12/2015 |

OTHER PUBLICATIONS

PCT/EP2016/062037 Written Opinion dated Nov. 28, 2017.

*Primary Examiner* — Angel R Estrada
(74) *Attorney, Agent, or Firm* — Arent Fox LLP

(57) ABSTRACT

A housing for a medical implant that includes a housing wall made of an electrically insulating material with an inner face and an outer face and an electrical transmission through the housing wall. The electrical transmission includes an electrically conductive first terminal contact surface disposed on the inner face of the housing wall, an electrically conductive second terminal contact surface disposed on the outer face of the housing wall, a capacitor integrated into the housing wall and that includes a first capacitor electrode and a second capacitor electrode, a first connection line that electrically connects the first terminal contact surface to the first capacitor electrode, and a second connection line that electrically connects the second terminal contact surface to the second capacitor electrode. No continuously electrically conductive connection exists between the first terminal contact surface and the second terminal contact surface.

18 Claims, 5 Drawing Sheets

(51) Int. Cl.
    *A61N 1/39* (2006.01)
    *H02J 50/05* (2016.01)
    *A61B 5/00* (2006.01)
    *A61N 1/378* (2006.01)
(52) U.S. Cl.
    CPC ............. *A61B 5/0031* (2013.01); *A61N 1/378* (2013.01); *A61N 1/3968* (2013.01); *H02J 50/05* (2016.02)
(58) Field of Classification Search
    CPC ......... A61B 5/0031; H02J 50/05; H02G 3/08; H02G 3/081
    USPC ............. 174/520, 50, 50.5, 50.52, 650, 659; 439/909; 607/4, 5, 36, 37; 361/302, 307, 361/306.3, 298.4, 299.5, 306.1, 600, 601
    See application file for complete search history.

(56) References Cited

U.S. PATENT DOCUMENTS

| | | | |
|---|---|---|---|
| 6,011,993 A | 1/2000 | Tziviskos et al. | |
| 6,768,629 B1 | 7/2004 | Allen et al. | |
| 8,604,341 B2 * | 12/2013 | Barry | A61N 1/3754 174/650 |
| 8,642,887 B1 * | 2/2014 | Li | A61N 1/3754 174/650 |
| 8,653,384 B2 * | 2/2014 | Tang | A61N 1/3754 174/650 |
| 9,126,053 B2 * | 9/2015 | Kempf | A61N 1/3754 |
| 9,306,318 B2 | 4/2016 | Reisinger | |
| 2011/0029036 A1 | 2/2011 | Yamamoto et al. | |
| 2012/0006576 A1 | 1/2012 | Barry et al. | |
| 2015/0136475 A1 | 5/2015 | Boutaud | |

* cited by examiner

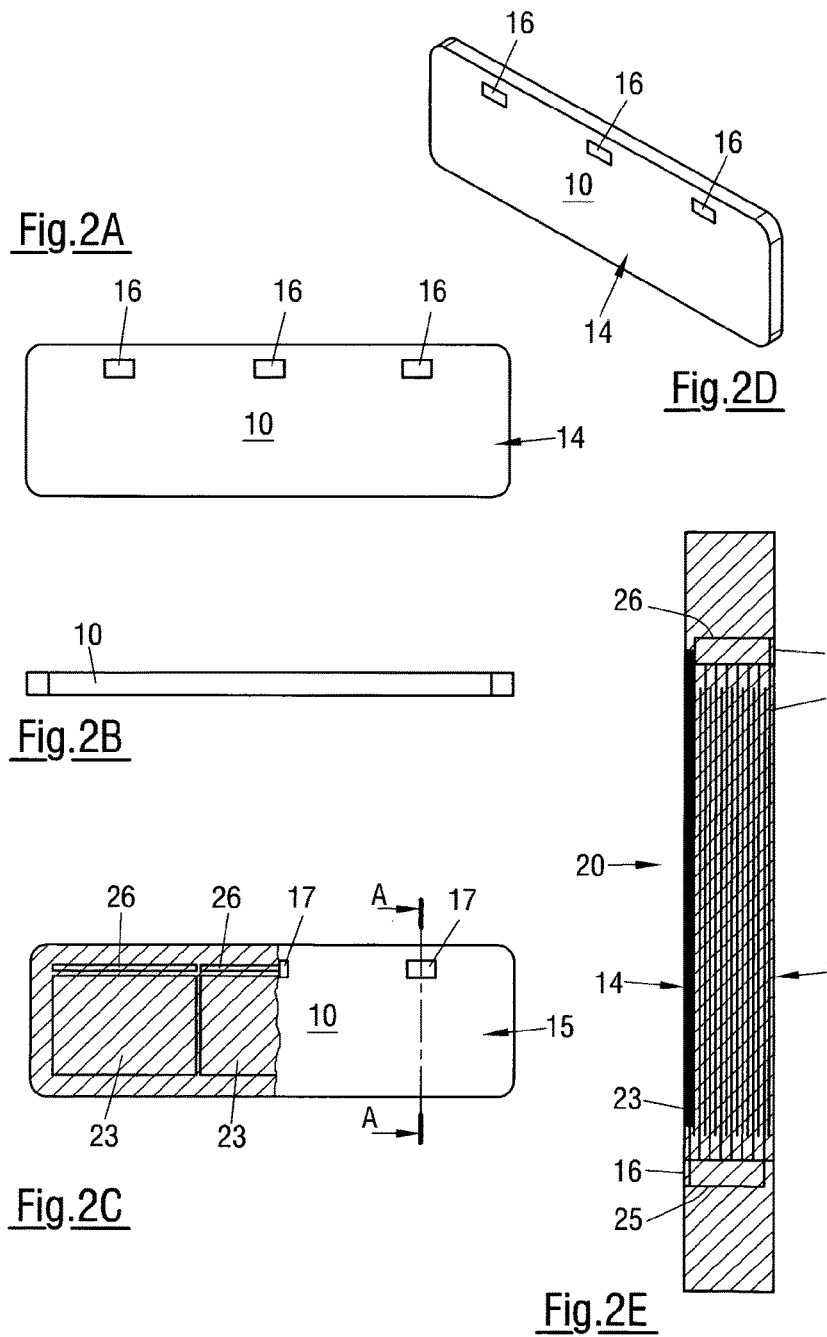

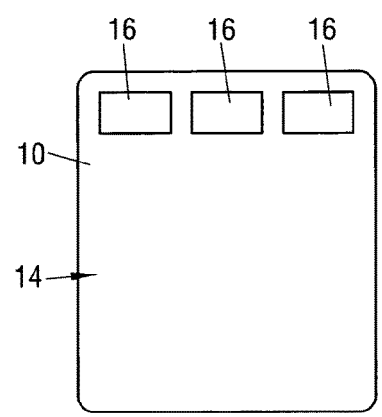
Fig.3A
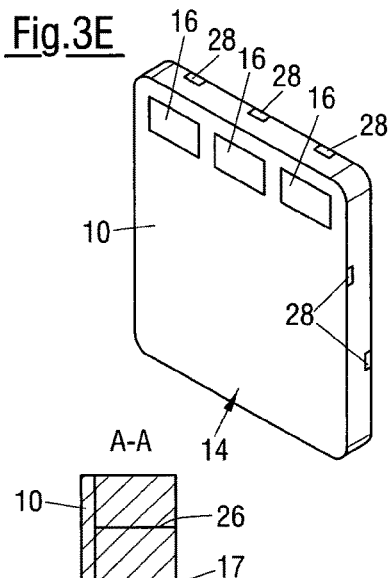
Fig.3E
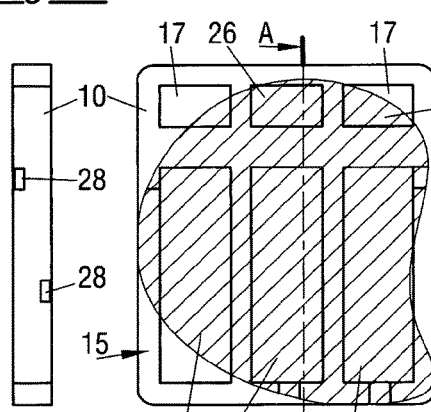
Fig.3B
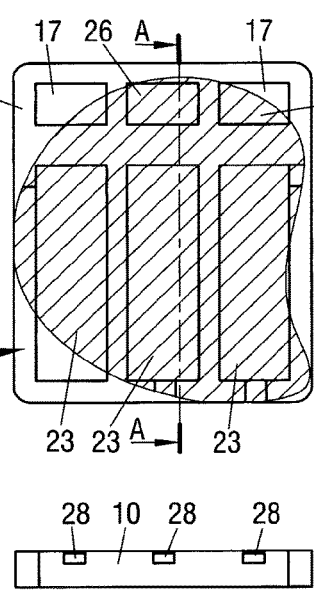
Fig.3C
Fig.3D
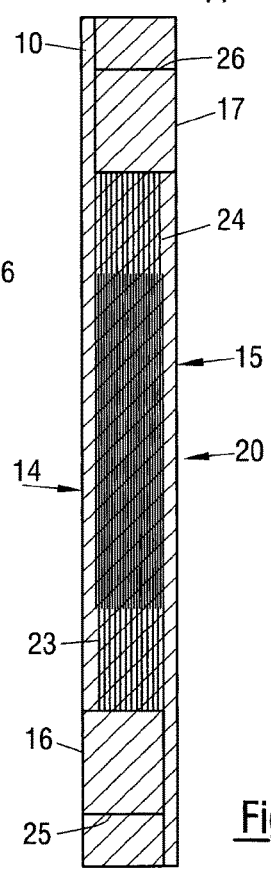
Fig.3F

HOUSING FOR A MEDICAL IMPLANT WITH AN ELECTRICAL TRANSMISSION

CROSS-REFERENCE TO RELATED APPLICATIONS

This application is a National Stage entry of International Application No. PCT/EP2016/062037, filed on May 27, 2016, which claims priority to German Patent Application No. 10 2015 108467.8, filed on May 28, 2015, the contents of each of these priority applications are hereby incorporated by reference in their entirety.

TECHNICAL FIELD

The present invention relates to a housing for a medical implant having an electrical transmission.

BACKGROUND

Diseases of the central nervous system such as epilepsy, Parkinson's disease or obsessive compulsive diseases are inter alia treated by means of direct electrical stimulation of the brain. For this purpose, electrodes are implanted into the target areas and are electrically connected to corresponding implant systems under the skin. Electrical stimuli are transmitted to the target area via the implant system. In electrical stimulation, in particular the observation of the charge density and thus of the charge amount per pulse is an important criterion to avoid long-term damage to the tissue in the course of the therapeutic stimulation. The transmission of the charge amount is typically limited by a coupling capacitor. One such coupling capacitor, e.g. having a capacitance of 100 nF and a charge transmission of a maximum of 1 µC is required per stimulation contact.

Single capacitors or an array of capacitors have previously typically been used for the implementation of the coupling capacitors. The capacitors are usually ceramic-based capacitors having a capacitance of 100 nF or more, for example. The value of the capacitance is substantially determined by the supply voltage of the implant and by the surface of the stimulation contacts. If a higher supply voltage or a smaller contact surface is selected, the capacitance can be selected as lower.

More recent electrode designs provide a larger number of electrode contacts, for example 8, 16 or 40 contacts. An implant to which such an electrode is connected accordingly has to have a large number of coupling capacitors. The coupling capacitors take up a large space within the implant due to their large number and therefore limit the miniaturization of the implant in order, for example, to select a favorable implantation site in the region of the cranium or to design the implant such that it is not visible from the outside. In addition, the risk of an inflammation reaction or of a rejection of the implant in the patient is the greater, the larger the implant is.

The large number of electrical contacts furthermore has to be led out of the interior of the hermetically closed implant housing. Such cable passages are frequently called "feedthroughs" in the technical literature. Conventional feedthroughs from the interior of the implant to the terminals of the electrode are typically realized by the integration of one or more ceramic components in openings of the housing that typically comprises titanium. The size and construction shape of the implant are hugely restricted by such feedthroughs. Furthermore, the location of the feedthrough represents a critical region that can be the site of a leak at which complications or even injury to the patient can occur due to the penetration of bodily fluids.

SUMMARY

It is therefore the underlying object of the invention to provide a housing for a medical implant that can be designed as smaller than conventional housings and offers the patient greater security. In addition, a corresponding implant and a manufacturing method for the housing should be provided.

The object underlying the invention is satisfied by the features of the independent claims. Advantageous further developments and aspects of the invention are set forth in the dependent claims.

A housing in accordance with the invention for a medical implant comprises a housing wall that is produced at least in part from an electrically insulating material. The housing wall has an inner side facing the interior space of the housing and an outer side facing the exterior space of the housing. A electrical transmission is guided through the housing wall. The electrical transmission extends from the inner side to the outer side of the housing wall. The electrical transmission assembly comprises an electrically conductive first terminal contact surface arranged at the inner side of the housing wall and an electrically conductive second terminal contact surface arranged at the outer side of the housing wall. A capacitor that has a first capacitor electrode and a second capacitor electrode is integrated into the housing wall. The electrically insulating material can be located between the first capacitor electrode and the second capacitor electrode and can serve as a dielectric for the capacitor. A first connection line electrically connects the first terminal contact surface and the first capacitor electrode to one another and a second connection line electrically connects the second terminal contact surface to the second capacitor electrode. There is only a capacitive electric coupling via the capacitor between the first terminal contact surface and the second terminal contact surface; there is no continuously electrically conductive connection, i.e. no direct electrically conductive connection, between the first terminal contact surface and the second terminal contact surface. The first terminal contact surface, the capacitor, and the second terminal contact surface are connected in series.

The first terminal contact surface is intended to be electrically connected to a device located within the housing. A control unit that generates electrical stimulation signals, in particular electrical current pulses, can, for example, be connected to the first terminal contact surface. The second terminal contact surface is intended to be electrically connected to a device located outside the housing. A stimulation electrode that serves for the application of the electrical stimulation signals generated by the control unit can, for example, be connected to the second terminal contact surface.

The capacitor connected to the first and second terminal contact surfaces represents both a capacitive electrical transmission through the housing wall and a coupling capacitor. Although there is no complete opening through the housing from the inner side to the outer side, an electrical transmission is nevertheless ensured by the capacitor so that electrical signals, for example from the interior of the housing, can be forwarded to a stimulation electrode located outside the housing. The transmitted charge amount is limited by the capacitor in this process.

The housing can have further capacitive electrical transmission assemblies that are built up in the same manner as the capacitive electrical transmission assembly described above.

It is possible to reduce the size of the implant with respect to conventional implants using the housing in accordance with the invention. Health risks for the patient, for example due to inflammation reactions or due to the rejection of the implant, can thereby be reduced. In addition, the implant can be implanted more easily in the region of the cranium. Since the capacitive electrical transmission additionally does not require a complete opening through the housing, it is easier to hermetically seal the housing so that no bodily fluids can penetrate into the housing that could damage the implant and that could result in a health risk for the patient.

The capacitor is preferably designed such that the first capacitor electrode has a plurality of first capacitor plates and the second capacitor electrode has a plurality of second capacitor plates and the first and second capacitor plates are arranged in alternating order above one another, i.e. the first and second capacitor plates engage into one another—like the teeth of two gears, for example. The electrically insulating material that servers as the dielectric for the capacitor is preferably located between the first and second capacitor plates. The first and second capacitor plates are aligned in parallel with one another and can in particular extend in parallel with the inner side and/or with the outer side of the housing wall.

In accordance with a preferred embodiment, the first connection line is electrically connected to the first capacitor plates and the second connection line is electrically connected to the second capacitor plates.

The invention allows any desired spacing to be selected between the first or second terminal contact surface and the capacitor. Provision can, for example, be made that the first terminal contact surface is partially or completely located outside a perpendicular projection of the capacitor onto the inner side of the housing wall and/or that the second terminal contact surface is partially or completely located outside a perpendicular projection of the capacitor onto the outer side of the housing wall.

It is not necessary that the total housing wall or even the total housing is produced from the electrically insulating material. It is sufficient if the region of the housing wall in which the capacitor is integrated comprises the electrically insulating material.

The electrically insulating material from which the housing wall or a part thereof is produced and that in particular serves as a dielectric of the capacitor is preferably a ceramic material. Titanium dioxide and barium titanate have proved to be particularly advantageous. These materials have high permittivity values. The ceramic material from which the housing wall or a part thereof is produced can largely or also completely comprise titanium dioxide or barium titanate.

The capacitor is preferably completely covered by the electrically insulating material. Only the first and second terminal contact surfaces are not covered by the electrically insulating material and can be used for contacting the capacitor.

The housing in accordance with the invention can advantageously be individually produced for a patient. In this case, the shape of the housing and in particular the shape of the housing wall can be adapted to the contour of the patient's skull.

A medical implant in accordance with the invention comprises a housing having the above-described features.

The implant can comprise a battery and a control unit that are surrounded by the housing. The battery serves for the power supply and the control unit can generate electrical signals that are led out of the housing via the capacitor. The control unit is connected to the first terminal contact surface formed at the inner side of the housing wall. The control unit can be connected to the first terminal contact surface by means of a suitable cable and/or a suitable adapter. The cable and/or the adapter can be directly connected to the first terminal contact surface.

A stimulation electrode can furthermore be provided that is connected to the second terminal contact surface formed at the outer side of the housing wall. The stimulation electrode can be connected to the second terminal contact surface by means of a suitable cable and/or a suitable adapter. The cable and/or the adapter can be directly connected to the second terminal contact surface.

The control unit is designed such that it generates stimulation signals that are transmitted to the stimulation electrode via the electrical transmission in order, for example, to stimulate tissue in the brain or spinal cord or myocardium of the patient.

A method of manufacturing a housing having the above-described features is furthermore provided in which the housing is manufactured with the aid of a 3D printing process.

The manufacturing method can comprise a plurality of ceramic powder layers being printed and a binder liquid being printed onto a respective ceramic powder layer to compact the ceramic powder.

An electrically conductive layer can furthermore be generated on at least one of the ceramic powder layers in that a first binder liquid that contains a first concentration of metal particles is printed onto the at least one ceramic powder layer.

To generate an electrical via through at least one of the ceramic powder layers, a second binder liquid can be printed onto this ceramic powder layer. The second binder fluid has a second concentration of metal particles that is lower than the first concentration of metal particles and that makes it possible for the second binder liquid to penetrate into the at least one ceramic powder layer. The viscosity of the second binder liquid can furthermore be lower than the viscosity of the first binder liquid.

Data on the contour of a patient's skull, in particular computer tomography data, can be advantageously used to adapt the shape of the housing to the contour of the patient's skull.

BRIEF DESCRIPTION OF THE DRAWINGS

The invention will be described in more detail in the following in an exemplary manner with reference to an embodiment and to the drawings. There are shown in these:

FIGS. 2A to 2E illustrate schematic representations of a part of a housing wall of a medical implant having a capacitive electrical transmission in accordance with a second embodiment;

FIGS. 3A to 3F illustrate schematic representations of a part of a housing wall of a medical implant having a capacitive electrical transmission in accordance with a third embodiment;

DETAILED DESCRIPTION

Figure 1:
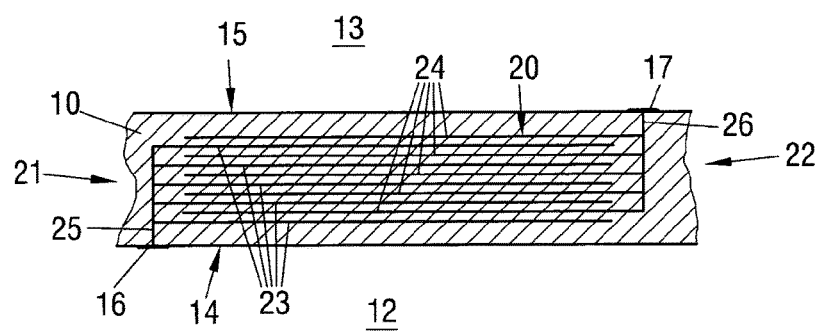
FIG. 1 illustrates a schematic representation of a part of a housing wall of a medical implant having a capacitive electrical transmission in accordance with a first embodiment.

FIG. 1 schematically shows a section through a housing wall 10 of a housing for a medical implant in accordance with a first embodiment. The inner region of the housing is marked by reference numeral 12 and the outer region of the housing is marked by reference numeral 13 in FIG. 1. Accordingly, a first side 14 is an inner side of the housing wall 10 and a second side 15 disposed opposite the first side 14 is an outer side of the housing wall 10.

A capacitive electrical transmission assembly that simultaneously serves as a coupling capacitor is integrated into the housing wall 10. The capacitive electrical transmission assembly comprises an electrically conductive first terminal contact surface 16 arranged at the inner side 14 and an electrically conductive second terminal contact surface 17 arranged at the outer side 15. In addition, the electrical transmission assembly comprises a capacitor 20 that is integrated into the housing wall 10 and that has a first capacitor electrode 21 and a second capacitor electrode 22.

The first capacitor electrode 21 comprises a plurality of first capacitor plates 23 and the second capacitor electrode 22 comprises a plurality of second capacitor plates 24. The first and second capacitor plates 23, 24 are thin electrically conductive layers that are arranged in alternating order above one another, i.e. a second capacitor plate 24 is arranged above a first capacitor plate 23 and a first capacitor plate 23 is in turn arranged above said second capacitor plate. The first and second capacitor plates 23, 24 are arranged in parallel with one another and in particular plane-parallel. The first and second capacitor plates 23, 24 in the present embodiment are furthermore arranged in parallel with the inner side 14 and/or with the outer side 15 of the part of the housing wall 10 in which the capacitor 20 is integrated.

The first and second capacitor plates 23, 24 are spaced apart from one another and do not contact one another. There is still no direct electrically conductive connection between the first capacitor plates 23 and the second capacitor plates 24. A ceramic material of which the part of the housing wall 10 shown in FIG. 1 is composed is located between the first and second capacitor plates 23, 24. The ceramic material located between the first and second capacitor plates 23, 24 represents the dielectric of the capacitor 20.

A first connection line 25 electrically connects the first terminal contact surface 16 to the first capacitor electrode 21. In the present embodiment, the first connection line 25 furthermore connects the first capacitor plates 23 to one another. In a corresponding manner, a second connection line 26 electrically connects the second terminal contact surface 17 to the second capacitor electrode 22. In the present embodiment, the second connection line 26 furthermore connects the second capacitor plates 24 to one another.

The first capacitor plates 23 extend perpendicular at least from that part of the first connection line 25 that connects the first capacitor plates 23 to one another. The second capacitor plates 24 extend perpendicular at least from that part of the second connection line 26 that connects the second capacitor plates 24 to one another.

The first and second connection lines 25, 26 extend perpendicular from the inner side 14 or from the outer side 15 into the housing wall 10.

The capacitor 20 is completely integrated into the housing wall 10 in the embodiment shown in FIG. 1, i.e. the first and second capacitor plates 23, 24 and the parts of the first and second connection lines 25, 26 that connect the first and second capacitor plates 23, 24 to one another are covered by the ceramic material from which the housing wall 10 is manufactured. None of the named components is exposed at the inner side 14 or at the outer side 15 of the housing wall 10. Only the first terminal contact surface 16 and the second terminal contact surface 17 are accessible from the internal region 12 or from the external region 13 of the housing.

The material from which the housing wall 10 or at least that part of the housing wall 10 in which the capacitive electrical transmission assembly is located is manufactured can contain titanium dioxide or barium nitrate, for example. Different electrically insulating materials that have a high permittivity would also be conceivable. Metals or meal alloys can be used as the materials for the electrically conductive components of the capacitive electrical transmission assembly.

The first and second connection lines 25, 26 allow the site of the first and/or second terminal contact surface(s) 16, 17 to be freely selected. The first and/or second terminal contact surface(s) 16, 17 does/do not necessarily have to be in the direct vicinity of the capacitor 20 integrated into the housing wall 10, but can also be arranged further remotely at the inner side 14 or at the outer side 15 of the housing wall 10.

The capacitance of a simple plate capacitor having only one capacitor plate per capacitor electrode is calculated according to the following equation:

$$C = \varepsilon_0 \cdot \varepsilon_r \cdot \frac{A}{d}, \tag{1}$$

where C indicates the capacitance of the capacitor; $\varepsilon_0$ the electrical field constant ($\varepsilon_0=8.85\times10^{-12}$ As/Vm); $\varepsilon_r$ the permittivity of the dielectric; A the overlapping surface of the capacitor electrodes; and d the spacing of the capacitor electrodes.

The following equation applies to the capacitor 20 shown in FIG. 1:

$$C = \varepsilon_0 \cdot \varepsilon_r \cdot \frac{(2 \cdot N - 1) \cdot A}{d}, \tag{2}$$

where C indicates the capacitance of the capacitor; $\varepsilon_0$ the electrical field constant ($\varepsilon_0=8.85\times10^{-12}$ As/Vm); $\varepsilon_r$ the permittivity of the dielectric; N the number of capacitor plates per capacitor plate; A the overlapping surface of the capacitor plates; and d the spacing of adjacent capacitor plates.

The capacitance C of the capacitor 20 integrated in the housing wall 10 can, for example, be varied by varying the surface values and spacings of the first and second capacitor plates 23, 24 so that a desired capacitance C of the capacitor 20, for example 100 nF, is reached.

The capacitance C of the capacitor 20 can be in the range of 20 to 1000 nF; exemplary values are 100 nF and 470 nF. The permittivity $\varepsilon_r$ of the dielectric can be in the range from 100 to 14,000. The permittivity $\varepsilon_r$ of titanium dioxide amounts to approximately 110; barium nitrate has a permittivity $\varepsilon_r$ between 1000 and 14,000. Each of the first and second capacitor electrodes 21, 22 can comprise 1 to 50, in particular 5 to 10, first or second capacitor plates 23, 24 respectively. The overlapping surface A of the capacitor plates 23, 24 is in a range from 0.1 to 25 mm². Capacitors having titanium dioxide as the dielectric typically have an overlapping surface A of the capacitor plates 23, 24 of 10 mm². 0.5 mm² is typically selected for capacitors having barium nitrate. The spacing d of adjacent first and second capacitor plates 23, 24 is in a range from 3 to 100 μm; 3 μm or 100 μm can be selected, for example. The thickness of the first and second capacitor plates 23, 24 is in a range from 1 to 20 μm and in particular in the range from 10 to 20 μm.

FIGS. 2A to 2E and FIGS. 3A to 3F show further embodiments of a housing wall of a medical implant having a capacitive electrical transmission. Mutually corresponding components are marked by the same reference numerals in FIGS. 1, 2A to 2E and 3A to 3F.

FIG. 2A shows a plan view of a part of the inner side 14 of a housing wall 10 in accordance with a second embodiment having three capacitive electrical transmission assemblies arranged next to one another. A side view of the housing wall 10 is shown in FIG. 2B and FIG. 2C shows the outer side 15 of the housing wall 10, with here a part of the housing wall 10 having been removed for illustration purposes to enable a plan view of a part of the capacitor 20. Accordingly, two first capacitor plates 23 and two second connection lines 26 can be seen in FIG. 2C. FIG. 2 shows a perspective view of the housing wall 10 and FIG. 2E shows a section through the housing wall 10 along the line A-A shown in FIG. 2C.

FIGS. 3A to 3F show a part of a housing wall 10 in accordance with a third embodiment having three capacitive electrical transmission assemblies arranged next to one another. The geometries of the first and second capacitor plates 23, 24 and of the first and second connection lines 25, 26 are slightly modified here with respect to the embodiment in accordance with FIGS. 2A to 2E. FIG. 3A shows a plan view of the inner side 14 of the housing wall 10 and FIG. 3B shows a plan view of the outer side 15 of the housing wall 10. FIG. 3 was created by a rotation of the view of FIG. 3A over the lower edge. A part of the housing wall 10 was removed in FIG. 3B for illustration purposes. FIGS. 3C and 3D show side views and FIG. 3E shows a perspective view of the housing wall 10. In addition, in FIGS. 3C to 3E, contact surfaces 28 are shown at side surfaces of the housing wall 10 that serve for test purposes. The conductivity of different individual capacitor plates 23, 24 can be measured using the contact surfaces 28. FIG. 3F shows a section through the housing wall 10 along the line A-A shown in FIG. 3B.

Figure 4:
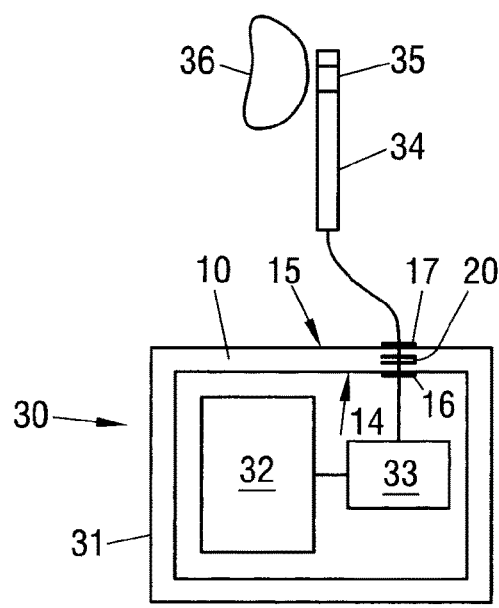
FIG. 4 illustrates a schematic representation of a medical implant having a capacitive electrical transmission in a housing wall.

FIG. 4 schematically shows an implant 30 that is intended to be surgically implanted into the body of a patient, for example in the region of the brain or of the spinal column or of the myocardium. The implant 30 comprises a hermetically sealed housing 31 as well as a battery 32 and a control unit 33 that are inserted into the housing 31.

A housing wall 10 of the housing 31 comprises a capacitive electrical transmission in accordance with one of the embodiments shown in FIGS. 1 to 3. The capacitive electrical transmission assembly inter alia includes a capacitor 20 integrated into the housing wall 10 as well as an electrically conductive first terminal contact surface 16 arranged at the inner side 14 of the housing wall 10 and an electrically conductive second terminal contact surface 17 arranged at the outer side 15 of the housing wall 10. The first terminal contact surface 16 is connected to the battery 32 and to the control unit 33 by means of suitable adapters and cables. The second terminal contact surface 17 is connected to a stimulation electrode 34 that has one or more stimulation contact surfaces 35 by means of suitable adapters and cables. The respective adapters and/or cables can be directly connected to the first and/or second terminal contact surface(s) 16, 17.

For illustration, only a capacitive electrical transmission assembly is shown in FIG. 4. However, further capacitive electrical transmission assemblies can naturally be integrated into the housing wall 10 or also into other walls of the housing 31 that are built up in the same way as the capacitive electrical transmission assemblies shown in FIG. 4.

During the operation of the implant 30, the control unit 33 generates the electric signals, in particular current pulses, that are forwarded to the stimulation electrode 34 via the capacitive electrical transmission in the housing wall 10. The stimulation electrode 34 applies the obtained electric signals as electrical stimuli to the tissue 36, for example of the brain or spinal cord, that is in contact with the stimulation contact surface 35.

Figure 5:
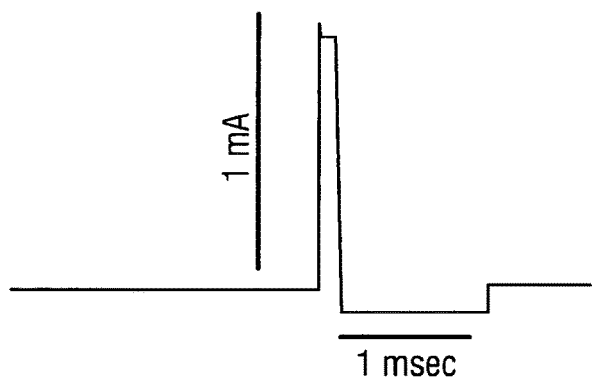
FIG. 5 illustrates a representation of an electrical current pulse used for stimulation.

FIG. 5 shows by way of example an electrical stimulus that can be applied with the aid of the implant 30. The current-controlled stimulus shown in FIG. 5 comprises an initial first pulse portion and a second pulse portion subsequent to it and flowing in the opposite direction. The amplitude of the first pulse portion is greater than the amplitude of the second pulse portion. The duration of the second pulse portion is in return longer than that of the first pulse portion. The two pulse portions are ideally dimensioned such that the charge that is transferred by them is the same in both pulse portions. In this case, exactly the same amount of charge is introduced into the tissue as is removed from the tissue.

The current progression shown in FIG. 5 was recorded after the capacitor 20. The capacitor 20 acts as a high pass filter by which DC current portions are suppressed.

The housing 31 as well as in particular the housing wall 10 can be manufactured using a 3D printing process. A process is, for example, suitable for this such as is described in document DE 10 2008 028 742 A1. The disclosure content of this document is included in the present application by reference.

In the manufacture of the housing 31 with the aid of a 3D printing process, a ceramic powder bed is first prepared that forms the base for the housing 31 to be manufactured. A binder liquid is printed onto the ceramic powder bed to compact the ceramic powder.

Electrically conductive structures, in particular the structures of the capacitor 20, are manufactured in that a binder liquid is printed onto the ceramic structure that contains metal particles, in particular silver particles. A binder liquid having a comparatively low concentration of silver particles and a comparatively low viscosity is used to manufacture vias such as the first and second connection lines 25, 26. This binder liquid is printed onto the ceramic structure and can penetrate into the not yet compacted ceramic powder. To manufacture horizontal electrically conductive structures such as the first and second terminal contact surfaces 16, 17 as well as the first and second capacitor plates 23, 24, a binder liquid having a higher concentration of silver particles is printed onto the ceramic structure and optionally onto the vias. The housing 31 can thus be produced by a repeated printing of ceramic powder layers and a subsequent printing of the desired binder liquids. Once all the desired ceramic layers have been printed and have been compacted with binder liquid, loose ceramic particles are first removed and then the housing 31 is sintered.

Figure 6A:
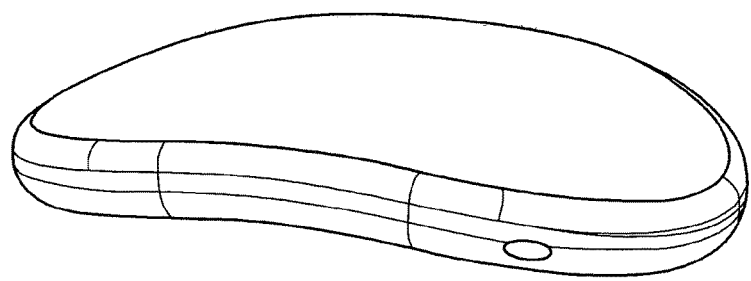
FIGS. 6A and 6B illustrate perspective representations of a housing for an implant adapted to the contour of a patient's skull.
Figure 6B:
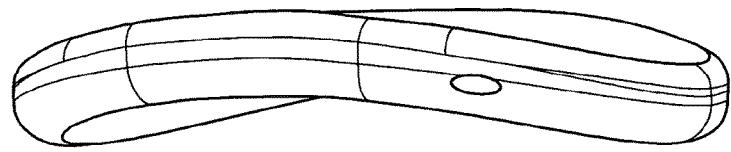

The 3D printing process allows the housing 31 to be individually adapted to any patient. For example, computer tomography data of the respective patient can be used to manufacture the housing 31 such that it is adapted to the contour of the patient's skull. Such a housing is shown by way of example in FIGS. 6A and 6B from different directions of view, with the housing here comprising an upper titanium plate that increases the strength of the housing and a lower ceramic part into which the capacitive electrical transmission assemblies are integrated.

The invention claimed is:

1. A housing for a medical implant, the housing comprising:
   a housing wall of an electrically insulating material having an inner side and an outer side; and
   an electrical transmission through the housing wall, wherein the electrical transmission comprises:
      an electrically conductive first terminal contact surface disposed at the inner side of the housing wall,
      an electrically conductive second terminal contact surface disposed at the outer side of the housing wall,
      a capacitor integrated into the housing wall and having a first capacitor electrode and a second capacitor electrode,
      a first connection line that electrically connects the first terminal contact surface to the first capacitor electrode, and
      a second connection line that electrically connects the second terminal contact surface to the second capacitor electrode, wherein there is no continuously electrically conductive connection between the first terminal contact surface and the second terminal contact surface.

2. The housing in accordance with claim 1, wherein the first capacitor electrode has a plurality of first capacitor plates and the second capacitor electrode has a plurality of second capacitor plates and the first and second capacitor plates are arranged in an alternating order above one another.

3. The housing in accordance with claim 2, wherein the first connection line is electrically connected to the first capacitor plates and the second connection line is electrically connected to the second capacitor plates.

4. The housing in accordance with claim 1, wherein the first terminal contact surface is located at least partially outside a projection of the capacitor onto the inner side of the housing wall.

5. The housing in accordance with claim 1, wherein the second terminal contact surface is located at least partially outside a projection of the capacitor onto the outer side of the housing wall.

6. The housing in accordance with claim 1, wherein the electrically insulating material comprises a ceramic material.

7. The housing in accordance with claim 6, wherein the electrically insulating material comprises titanium dioxide or barium nitrate.

8. The housing in accordance with claim 1, wherein the capacitor is completely covered by the electrically insulating material.

9. The housing in accordance with claim 1, wherein the housing comprises a shape that is adapted to a contour of a skull of a patient.

10. The housing in accordance with claim 9, wherein the housing wall comprises a shape that is adapted to the contour of the skull of the patient.

11. A medical implant having a housing comprising:
    a housing wall of an electrically insulating material having an inner side and an outer side; and
    an electrical transmission through the housing wall, wherein the electrical transmission comprises:
       an electrically conductive first terminal contact surface disposed at the inner side of the housing wall,
       an electrically conductive second terminal contact surface disposed at the outer side of the housing wall,
       a capacitor integrated into the housing wall and having a first capacitor electrode and a second capacitor electrode,
       a first connection line that electrically connects the first terminal contact surface to the first capacitor electrode, and
       a second connection line that electrically connects the second terminal contact surface to the second capacitor electrode, wherein the first terminal contact surface is not continuously electrically connected to the second terminal contact surface.

12. The medical implant in accordance with claim 11, wherein the housing comprises a battery and a control unit integrated therein, with the control unit connected to the first terminal contact surface.

13. The medical implant in accordance with claim 12, further comprising a stimulation electrode connected to the second terminal contact surface, wherein the control unit is configured to generate stimulation signals that are transmitted to the stimulation electrode by the electrical transmission.

14. A method of manufacturing a housing for a medical implant having a housing, the method comprising:
    forming, using a 3D printing process, a housing wall of an electrically insulating material having an inner side and an outer side; and
    providing an electrical transmission through the housing wall, wherein the electrical transmission comprises:
       an electrically conductive first terminal contact surface disposed at the inner side of the housing wall,
       an electrically conductive second terminal contact surface disposed at the outer side of the housing wall,
       a capacitor integrated into the housing wall and having a first capacitor electrode and a second capacitor electrode,
       a first connection line that electrically connects the first terminal contact surface to the first capacitor electrode, and
       a second connection line that electrically connects the second terminal contact surface to the second capacitor electrode, wherein the first terminal contact surface is not continuously electrically connected to the second terminal contact surface.

15. The method in accordance with claim 14, further comprising:
    printing a plurality of ceramic powder layers; and
    printing a binder liquid onto a respective ceramic powder layer to compact the ceramic powder.

16. The method in accordance with claim 15, further comprising printing a first binder liquid containing a first concentration of metal particles onto at least one of the ceramic powder layers to generate an electrically conductive layer on the at least one ceramic powder layer.

17. The method in accordance with claim 16, further comprising printing a second binder liquid containing a second concentration of metal particles onto at least one of the ceramic powder layers to produce an electrical via through the at least one ceramic powder layer, wherein the first concentration of metal particles is higher than the second concentration of metal particles.

18. The method in accordance with claim 14, further comprising adapting a shape of the housing to a contour of a skull of the patient.

\* \* \* \* \*